US012806355B2

(12) United States Patent
Enk et al.

(10) Patent No.: US 12,806,355 B2
(45) Date of Patent: Nov. 24, 2026

(54) VENTILATOR AND METHOD FOR DETERMINING AT LEAST ONE ALVEOLAR PRESSURE AND/OR A PROFILE OF AN ALVEOLAR PRESSURE IN A RESPIRATORY TRACT OF A PATIENT

(71) Applicant: International Emergency Services SL, Derio (ES)

(72) Inventors: Dietmar Enk, Coesfeld (DE); Thomas Heinrich Barnes, Warlingham (GB)

(73) Assignee: International Emergency Services SL, Derio (ES)

( * ) Notice: Subject to any disclaimer, the term of this patent is extended or adjusted under 35 U.S.C. 154(b) by 907 days.

(21) Appl. No.: 18/015,647

(22) PCT Filed: Jun. 2, 2021

(86) PCT No.: PCT/EP2021/064749
§ 371 (c)(1),
(2) Date: Jan. 11, 2023

(87) PCT Pub. No.: WO2022/012812
PCT Pub. Date: Jan. 20, 2022

(65) Prior Publication Data

US 2023/0248929 A1 Aug. 10, 2023

(30) Foreign Application Priority Data

Jul. 14, 2020 (DE) ..................... 10 2020 118 529.4

(51) Int. Cl.
*A61M 16/00* (2006.01)

(52) U.S. Cl.
CPC ... *A61M 16/026* (2017.08); *A61M 2016/0027* (2013.01); *A61M 2230/42* (2013.01)

(58) Field of Classification Search
CPC ........ A61M 16/026; A61M 2016/0027; A61M 2230/42; A61M 16/024; A61M 2205/3344; A61M 16/0045; A61M 2230/46
See application file for complete search history.

(56) References Cited

U.S. PATENT DOCUMENTS

2011/0060237 A1 3/2011 Kurosawa et al.
2019/0022342 A1* 1/2019 Enk ..................... A61M 16/024
2019/0298947 A1* 10/2019 Trivikram ............ A61H 9/0078

FOREIGN PATENT DOCUMENTS

CN 109803708 A 5/2019
DE 102007013385 A1 9/2008
(Continued)

OTHER PUBLICATIONS

Jean-Luc Diehl, Daniel Isabey, Gilbert Desmarais, Laurent Brochard, Alain Harf, and Frã © dã © ric Lofaso; Journal of Applied Physiology 1999 87:1, 428-437 DOI: 10.1152/jappl.1999.87.1.428 Accessed Jan. 7, 2026 (Year: 1999).*
(Continued)

*Primary Examiner* — Kendra D Carter
*Assistant Examiner* — Keira Eileen Callison
(74) *Attorney, Agent, or Firm* — Young Basile Hanlon & MacFarlane, P.C.

(57) ABSTRACT

The invention relates to a ventilator (1), at least comprising a gas supply device (2) and a gas discharge device (3), for supplying a first fluid flow (4) to a respiratory tract (5) of a patient and for discharging a second fluid flow (6) from the respiratory tract (5) back into the ventilator (1) or to a surrounding area (7); a pressure sensor (8) for sensing a pressure (9) in the respiratory tract (5); and a control device (10) for operating the ventilator (1) and for determining an alveolar pressure $P_{alv}$ (9) and/or a profile of an alveolar pressure $P_{alv}$ (9) of a respiratory tract (5) of a patient. The
(Continued)

Figure 1:
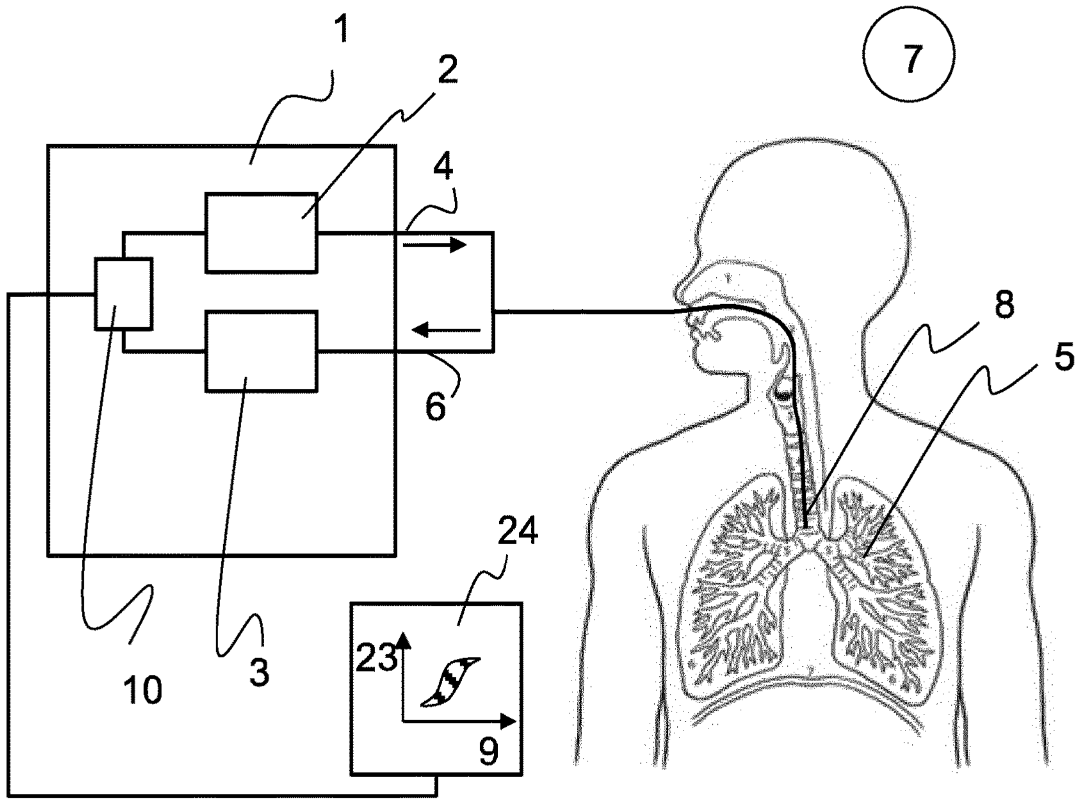

invention also relates to a method for determining at least one alveolar pressure $P_{alv}$ (9) and/or a profile of an alveolar pressure $P_{alv}$ (9) of a respiratory tract (5) of a patient with a ventilator (1).

18 Claims, 2 Drawing Sheets

(56) References Cited

FOREIGN PATENT DOCUMENTS

| | | | |
|---|---|---|---|
| DE | 102016103678 | | 9/2017 |
| DE | 102016109528 | A1 | 9/2017 |
| WO | 2007092492 | A2 | 8/2007 |
| WO | 2017148639 | A1 | 9/2017 |
| WO | 2017194915 | A1 | 11/2017 |

OTHER PUBLICATIONS

Kaczka DW, Dellaca RL. Oscillation mechanics of the respiratory system: applications to lung disease; DOI: 10.1615/CritRevBiomedEng.v39.i4.60 Accessed Jan. 7, 2026 (Year: 2011).*

Kaczka, David W., and Raffaele L. Dellaca. "Oscillation Mechanics of the Respiratory System: Applications to Lung Disease." Critical Reviews in Biomedical Engineering, vol. 39, No. 4, 2011, pp. 337-359., https://doi.org/10.1615/critrevbiomedeng.v39.i4.60.

Stankiewicz, Barbara, et al. "A New Infant Hybrid Respiratory Simulator: Preliminary Evaluation Based on Clinical Data." Medical and Biological Engineering and Computing, vol. 55, No. 11, Mar. 25, 2017, pp. 1937-1948., https://doi.org/10.1007/s11517-017-1635-9.

Marchal, F, et al. "Forced Oscillations, Interrupter Technique and Body Plethysmography in the Preschool Child." Paediatric Respiratory Reviews, vol. 6, No. 4, Dec. 1, 2005, pp. 278-284., https://doi.org/10.1016/j.prrv.2005.09.007.

Schumann, S et al. "Determination of respiratory system mechanics during inspiration and expiration by FLow-controlled EXpiration (FLEX): a pilot study in anesthetized pigs." Minerva anestesiologica vol. 80,1 (2014): 19-28.

International Search Report, PCT Application No. PCT/EP2021/064749, mailed Sep. 13, 2021 (3 pages).

* cited by examiner

VENTILATOR AND METHOD FOR DETERMINING AT LEAST ONE ALVEOLAR PRESSURE AND/OR A PROFILE OF AN ALVEOLAR PRESSURE IN A RESPIRATORY TRACT OF A PATIENT

This application is a U.S. national stage application of International Application no. PCT/EP2021/064749, filed Jun. 2, 2021, which claims the benefit of the filing date of German Application No. 10 2020 118 529.4, filed Jul. 14, 2020.

The invention relates to a ventilator and a method for ascertaining or determining indices or at least a (global) alveolar pressure or a plot of an alveolar pressure (in the alveoli) in an airway of a patient, optionally additionally for ascertaining or determining an airway-related resistance and/or a tissue-related resistance.

Peak inspiratory pressure (PIP) refers to the highest positive pressure [in mbar, i.e., millibars] that is artificially generated in the airway during inhalation (inspiration).

End-inspiratory (plateau) pressure is the pressure that is measured in the airway at the end of inspiration.

End-expiratory (plateau) pressure, which is maintained in the airway after completion of exhalation (expiration), is preferably positive and is therefore also referred to as positive end-expiratory pressure (PEEP). In the following, reference is always made to PEEP.

Compliance [in ml/mbar, i.e., milliliters/millibar] is a measure of the expandability or compression resilience of the lung/thorax system of a patient.

Under ventilation conditions, so-called static compliance is calculated by using tidal volume ($V_T$) [in ml], which refers to the volume of air supplied during an inspiration, and the difference between end-inspiratory (plateau) pressure (e.g., $P_{I1}$) and end-expiratory (plateau) pressure (e.g., $P_{E1}$).

By contrast, so-called dynamic compliance is calculated on the basis of $V_T$ and the difference between PIP (e.g., $P_{I2}$) and PEEP (e.g., $P_{E2}$) [in mbar]. The pressure difference is therefore regularly greater in the case of dynamic compliance or at least as great as the pressure difference in the case of static compliance. Since compliance generally exhibits a changing relationship between pressure (P) and volume (V)—as pressure and volume change—it appears as a curve on a pressure-volume diagram.

Compliance thus indicates how much fluid (e.g., respiratory gas, i.e., a volume of air), i.e., a delta V, is introduced into the at least one airway or removed from the airway, such that a pressure in the airway changes by a pressure difference delta P. During at least one ventilation process (comprising an inspiration process, i.e., the supply of fluid into the airway, and an expiration process, i.e., the discharge of fluid from the airway), a plot of the compliance curve can be ascertained or additionally estimated (e.g., on the basis of empirical values). What can be ascertained in particular is the section of the compliance curve in which a certain volume (possibly $V_T$) can be supplied in a smallest possible pressure interval.

A user or preferably an (automatically operating) control device of a ventilator can thus, taking into account an ascertained or additionally estimated plot of at least a section of a compliance curve in a pressure-volume diagram, determine a position of a pressure interval having the pressures $P_I$ and $P_E$ and then set these pressures on the ventilator (e.g., PIP as $P_I$ and PEEP as $P_E$), so that at least a ventilation process, i.e., an inspiration and/or an expiration, occurs between these pressures $P_I$ and $P_E$ and an absolute value of the compliance of this ventilation process is as large as possible.

Continuous ventilation should be set in such a way that a minute volume (i.e., $V_T$·ventilation frequency [/min, i.e., ventilation processes per minute]) necessary for normoventilation (i.e., the adequate elimination or exhalation of carbon dioxide) is as small as possible and can be supplied and discharged at maximum possible compliance.

In contrast to static compliance, dynamic compliance must also take into account the resistances (in the broadest sense) to be overcome during inspiration or expiration, including effects of so-called ventilation history (i.e., how the lung was ventilated). The latter arises from the fact that the lung is a viscoelastic organ, the mechanical properties of which depend on how it is or was moved.

Resistance (measured in mbar/l/s; i.e., millibars/liter/second or mbar·s/l, i.e., millibar·second/liter) describes the resistances to be overcome during inspiration or expiration and indicates the pressure necessary for gas flow (fluid flow) and hence volume change (in the lung) per time.

In a ventilated patient, resistance is typically estimated during inspiration by measuring the pressure difference between peak inspiratory pressure (PIP) and end-inspiratory (plateau) pressure in relation to mean inspiratory flow (inspiratory fluid flow). The measurement (hitherto) requires a stop in the inspiratory flow.

For example, a pressure difference between peak inspiratory pressure ($P_{I2}$) and end-inspiratory (plateau) pressure ($P_{E2}$) of 2 mbar at a mean inspiratory flow of 18 l/min [liters/minute] yields an (inspiratory) resistance of 6.67 mbar/l/s; i.e., 2 mbar/18 l/min or 2 mbar 60 s/18 l.

In conventional ventilators, resistance is usually determined by this method. In addition, there are various other methods for determining resistance that are based on intermittent or superimposed measurements.

In order to be able to fully capture and describe the properties of a ventilated lung, it is desirable not only to precisely measure dynamic compliance, but also to accurately determine inspiratory and expiratory resistance. This is required in order to be able to ventilate especially critically ill patients (whose lungs are affected) in a personalized manner and as gently as possible in the region of optimal compliance, i.e., between a so-called lower inflection point, at which compliance maximally increases during inspiration in terms of optimal recruitment of the lung tissue, and a so-called upper inflection point, at which compliance maximally decreases during inspiration owing to increasing overstretching in the lung tissue.

However, resistance arises not only from the gas flow-dependent resistance of the airways (airway-related; e.g., cross-section of the airways, turbulence), but also from resistances in the tissue (tissue-related; e.g., due to shearing, friction, viscoelasticity, possibly due to mass inertia).

Mass inertia effects play a role especially at the start of inspiration and expiration, when tissue (both the lung itself and the surrounding/adjacent tissue) has to be accelerated and decelerated owing to the increase or decrease in lung volume. Shearing can occur within (especially functionally inhomogeneous) lung tissue (so-called "shear stress"), whereas friction can occur at interfaces such as, for example, the sliding layer of the outer and inner pulmonary pleurae (pleura parietalis and pleura visceralis), which moreover increases in (surface) size during inspiration and decreases in (surface) size during expiration. Viscoelastic effects arise, inter alia, from a differing blood volume in the pulmonary vascular system during inspiration and expiration, making the lung differently resistive.

Within the lung, there are not only differently compliant (expandable) lung compartments, but there are also, with regard to resistance, lung compartments which have a lower or higher airway-related or tissue-related resistance. This inevitably means that an external observer only ever sees a global picture of compliance and resistance.

However, differentiation of resistance into an airway-related component and tissue-related component is of clinical interest: On the basis of the airway-related component, it is possible in principle to calculate the (global) alveolar pressure plot (in the alveoli). Moreover, an increased airway-related resistance (in contrast to the tissue-related component) is amenable to drug therapy. By contrast, tissue-related resistance points to changes in the (lung) tissue. Thus, tissue-related resistance can be used as a diagnostic, therapeutic or even prognostic parameter.

In the literature, the proportion of the tissue-related resistance in the (total) resistance measured at peak (inspiratory) pressure is estimated at about 25%, i.e., about 75% of the (total) resistance is attributable to the airway-related component. These data are usually based on invasive measurement methods (e.g., esophageal pressure measurements).

It is an object of the present invention to solve (at least in part) the problems cited with regard to the prior art. In particular, a ventilator and a method for determining indices or at least a (global) alveolar pressure or a plot of an alveolar pressure (in the alveoli) in an airway of a patient, optionally additionally for ascertaining or determining an airway-related resistance and/or a tissue-related resistance, by means of a ventilator, shall be proposed. In particular, a ventilator by means of which indices are definable and determinable shall be proposed.

A ventilator having the features as claimed in claim 1 and a method having the features as claimed in claim 15 contribute to achieving these objects. Advantageous developments are the subject matter of the dependent claims. The features individually stated in the claims are combinable with one another in a technologically feasible manner and can be supplemented by explanatory facts from the description and/or details from the figures, showing further embodiment variants of the invention.

There is proposed a ventilator, at least comprising a gas supply device and a gas discharge device, for supplying an (inspiratory) fluid flow to an airway of a patient and for discharging an (expiratory) fluid flow from the airway (of the patient) back into the ventilator or to an environment, a pressure sensor for sensing a pressure in the airway, and a control device for operating the ventilator.

In particular, a fluid flow is adjustable to a predeterminable value at least during an inspiration process and an expiration process.

The control device is configured to operate the ventilator and to carry out a method, especially a measurement and calculation method, comprising at least the following steps:

a) defining a pressure interval in which the patient is to be ventilated for a defined time interval;
b) repeatedly and alternately carrying out one inspiration process at a time with a first fluid flow $Q_1$ by means of the gas supply device and one expiration process at a time with a second fluid flow $Q_2$ by means of the gas discharge device within the pressure interval,
c) sensing the fluid flows and the pressure which changes during step b);
d) carrying out a Fourier transform for the sensed values of the pressure and forming a first frequency spectrum for the pressure and carrying out a Fourier transform for the sensed values of the fluid flows and forming a second frequency spectrum for the fluid flows;
e) calculating an impedance $Z_{aw}$ of the airway by dividing the first frequency spectrum by the second frequency spectrum, wherein the impedance comprises a real component $Real(Z_{aw})$ and an imaginary component $Im(Z_{aw})$;
f) modeling at least the real component by a first mathematical model and ascertaining an alveolar pressure or a plot of an alveolar pressure.

In particular, in the case of the ventilator proposed here, the patient is ventilated solely via the ventilator. In particular, the fluid flow is thus admitted to the airway of the patient solely via the ventilator (during inspiration and expiration). In particular, there is thus no fluid flow that is not initiated or generated by the ventilator. In particular, the ventilator comprises for this purpose a lumen for inspiration and a lumen for expiration. In particular, a common lumen (e.g., a ventilation catheter) is provided, so that the fluid flow is supplied to the airway or discharged from the airway only through one lumen.

In particular, the pressure sensor is arranged endotracheally (i.e., in the trachea). This makes it possible to ascertain the pressure inside the airway of the patient.

In particular, the pressure sensor is arranged at the distal end of a ventilation catheter, which is located in the airway of the patient as part of the ventilator.

The pressure sensor can optionally also be arranged at a distance from the patient, instead of endotracheally. The tracheal pressure should then be mathematically determinable. However, such an arrangement of the pressure sensor can give rise to inaccuracies which can impair the measurements described here.

In particular, the ventilation catheter has a dead space volume (i.e., the volume remaining in the ventilation catheter during an inspiration or expiration process) of at most 100 ml, in particular of at most 50 ml.

In particular, the values of the pressure and the fluid flows that are sensed in step c) are sensed solely on the basis of the ventilation process (comprising an inspiration process and an expiration process), i.e., in particular, there is no additional stimulation or change of the pressure or the fluid flows by a device not serving solely for ventilation.

For example, it is known that the airway or a ventilator can be stimulated by a signal, so that fluctuations of the pressure within the airway that are caused as a result can be sensed. However, this stimulation occurs outside the actual ventilation process, i.e., not while there is a fluid flow. Furthermore, the generation of the signal requires that a separate device be provided or requires additional equipment complexity.

In particular, it is taken into account here that, for example, an airway-related resistance and a tissue-related resistance change differently with respect to a ventilation frequency. It can be assumed in particular that, for example, the airway-related resistance is substantially independent of the ventilation frequency, i.e., does not change as ventilation frequency changes.

In particular, frequency spectra are formed here for the sensed values of the pressure and the fluid flows, i.e., the values sensed in step c) in the time domain are transformed as part of step d) by a Fourier transform into the frequency domain.

The quality of this transformation can be influenced especially by the type of ventilation. Certain ventilation methods and ventilators configured for said ventilation methods are therefore particularly advantageously suitable for carrying out this method.

As part of step e), an impedance can be calculated from the frequency spectra. It comprises in particular a real component and an imaginary component, i.e., it is a complex quantity. Said calculated impedance or the plot thereof over frequency, in particular the real component thereof, can in particular be modeled as part of step f) by a first mathematical model.

If the plot has been modeled by the first mathematical model, for example with a predeterminable accuracy, it is possible to read certain parameters or indices from the first model. In particular, the alveolar pressure or the plot thereof can be determined at least from the real component.

In particular, the first model comprises the equation $\mathrm{Real}(Z_{aw})=R_{aw}+G/\omega^{\alpha}$, with $R_{aw}$: airway-related resistance;

$G/\omega^{\alpha}$: tissue-related resistance; with G as a constant, ω as the angular frequency (i.e., 2×π×frequency of ventilation) and α as a constant; wherein the real component describes the resistance, i.e., the resistances to be overcome during inspiration or expiration.

Said angular frequency ω is in particular the ventilation frequency (i.e., the number of ventilation processes per unit of time during step b)) multiplied by the factor 2×π.

The plot of the real component of the impedance calculated according to step e) can in particular be mathematically modeled by the indices or parameters of the first model. Known approximation methods can be used here.

In particular, the alveolar pressure $P_{alv}$ or the plot thereof is ascertained from the equation $P_{alv}=P_{trach}-Q_i \times R_{aw}$, with $Q_i$: the current fluid flow during step b).

The measured or determined pressure $P_{trach}$ is the pressure in the airway that changes over time. The plot of the pressure $P_{alv}$ over time thus arises as a function of the pressure $P_{trach}$ that changes over time.

It has been observed that the (total) resistance, i.e., the sum total of airway-related resistance and tissue-related resistance, increases when $V_T$ increases but gas inflow is the same, presumably due to an increase in the tissue-related resistance. This seems plausible for the following reason: the small pressure drop from the small bronchi or bronchioles (having smooth muscles), which largely determine the airway-related resistance, to the alveoli makes it possible to assume an airway-related resistance largely independent of the ventilation pressures, since higher pressures in the small bronchi or bronchioles (having smooth muscles) are also necessarily associated with higher pressures in the dependent alveoli surrounding the small bronchi or bronchioles (having smooth muscles).

In particular, however, the airway-related resistance seems to decrease slightly during the inspiration process. This can be explained by a cross-sectional enlargement (though small) of the bronchi with increasing pressure, which more than compensates for the resistance-increasing effect of an increasing length of the small bronchi or bronchioles (having smooth muscles) during inspiration. In this regard, reference is made to the Hagen-Poiseuille equation, which states that changes in radius affect gas flow (fluid flow) to the fourth power, but changes in length affect gas flow (fluid flow) only proportionally.

Even if the size of the pressure drop from the small bronchi or bronchioles (having smooth muscles) to the alveoli is necessarily gas flow-dependent, and a relatively greater expansion and hence cross-sectional enlargement of the small bronchi or bronchioles (having smooth muscles) can thus occur at higher gas flows, higher airway pressures thus lead at most to a decrease, but not an increase, in the airway-related resistance.

It can therefore be plausibly assumed that the increase in the inspiratory (total) resistance at higher tidal volumes but at the same gas inflow (fluid flow during inspiration) is largely based on an increase in the tissue-related resistance. Conversely, one can expect that, in the case of an expiratory outflow of the respiratory gas (fluid flow during expiration) and a thereby decreasing lung volume, the proportion of the tissue-related resistance in the (total) resistance decreases again and eventually (virtually) disappears in the case of complete expiration or reaches a minimum in the case of PEEP.

In particular, the imaginary component is also modelable in step f) by a second mathematical model, wherein the second model comprises the equation $$Z_{aw}=R_{aw}+k\times j\times\omega\times I_{aw}+\frac{G-j\times H}{\omega^{\alpha}};\text{ where}$$

$$\mathrm{Im}(Z_{aw})=j\times\left(k\times\omega\times I_{aw}+\frac{-H}{\omega^{\alpha}}\right);$$

with k: a constant;

$I_{aw}$: inertia of the airway;

$-H/\omega^{\alpha}$: resilience of the airway with H as a constant;

wherein the imaginary component describes the airway reactance $X_a$, wherein a compliance of the airway is described by $$C=-\frac{1}{\omega\times X_a}.$$

The imaginary component should in particular not be ascertained for the determination of the alveolar pressure or the plot thereof. However, other parameters that may be considered relevant can be derived from the imaginary component, for example airway reactance and compliance of the airway.

In particular, the pressure sensor is arranged endotracheally.

In particular, at least steps a) to c) are carried out in different pressure intervals. This results in additional measurement values that are taken into account in the frequency spectra. In particular, it is thus possible to determine more accurately the alveolar pressure or the plot thereof as a function of the pressure present in the airway.

In particular, the pressure interval is set in such a way that normoventilation is possible in this pressure interval.

Normoventilation comprises ventilation by means of which a patient can be ventilated for an unlimited period of time. What are thus supplied and discharged are fluid flows or volumes through which the patient is permanently sufficiently ventilated.

It is preferred that the pressure interval is reduced at least for a time interval, the method being carried out within said time interval.

In particular, steps a) to c) are carried out repeatedly, i.e., multiple different pressure intervals are defined one after the other and values for pressure and fluid flows are then sensed in said pressure intervals according to step c). Said values from different pressure intervals are then further processed in steps d) to f).

In particular, the pressure interval encompasses at most 10 mbar, especially at most 5 mbar, preferably at most 2 mbar. In particular, the pressure interval encompasses at least 1 mbar, preferably at least 2 mbar.

In particular, the fluid volume supplied and/or discharged within the pressure interval (and within one ventilation process) is at most 10%, preferably at most 5%, particularly preferably 2%, of a maximum volume of the airway. In particular, the fluid volume is at least 1%, preferably at least 2%, of the maximum volume of the airway.

Thus, if a maximum volume (largest volume of an airway without it being damaged by expansion) is 2000 ml, what is supplied and/or discharged here is a fluid volume of at most 200 ml.

In particular, at least five, preferably at least seven, particularly preferably at least 10, inspiration processes and expiration processes are carried out in step b).

In particular, values for the pressure and the fluid flow are sensed at the same time points in each case in step c) and the time points have time intervals of at most 0.1 seconds, preferably at most 0.05 seconds, particularly preferably at most 0.01 seconds. In particular, the time points have time intervals of at least 0.005 seconds, preferably at least 0.01 seconds.

In particular, the ventilator is suitably designed for sole ventilation of the patient; wherein normoventilation of the patient is performable via the control device at least before step a) or after step c).

In particular, the ventilator comprises a suction device, so that in step b) the second fluid flow is at least partially generated by suction in at least an expiration process.

In particular, passive expiration takes place in known ventilators, meaning that a second fluid flow may not be accurately sensible. In particular, the present ventilator is designed in such a way that the fluid flows are accurately determinable at any time point and/or are adjustable by the ventilator at any time point.

A suction device can ensure in particular that a constant fluid flow throughout an expiration process can be maintained, even toward the end of the expiratory process, i.e., until a PEEP for example is reached.

In particular, the fluid flow is adjustable to a constant value at least during an inspiration process and an expiration process, wherein the first fluid flow $Q_1$ and the second fluid flow $Q_2$ are both constant during step b).

In particular, the fluid flows set in each case vary by at most 30%, preferably by at most 20%, particularly preferably by at most 10%. Very particularly preferably, the fluid flows each only vary by at most 5% or are even constant.

Constant means in particular that the fluid flows vary by less than 5%, preferably by less than 1%.

In particular, the ventilation according to step b) is done solely with constant fluid flows. In particular, no pauses are intended between the inspiration process and the expiration process; this means that the inspiration processes and expiration processes immediately follow one another.

In particular, the fluid flows are of equal size, i.e., the (inspiratory) first fluid flow and the (expiratory) second fluid flow are equal in absolute value.

Adjusting the fluid flows, in particular to constant fluid flows, can increase the accuracy of the proposed method. In particular, it is thus possible to generate suitable frequency spectra from which the impedance is determinable with high precision. The modeling of the components of the impedance by the mathematical models can thus be done with high accuracy, meaning that the parameters determinable by the method can be calculated with high accuracy.

For very precise ascertainment of the mentioned indices or parameters (i.e., for example alveolar pressure, airway-related resistance and tissue-related resistance, etc.), the following is especially necessary or useful:

i. gas flow (fluid flow) during inspiration (inspiration process) and expiration (expiration process) that is relatively stable or relatively constant and is especially equal in absolute value;
ii. ideally tracheal (inside the trachea) measurement of the pressure during inspiration;
iii. ideally tracheal (inside the trachea) measurement of the pressure during expiration.

Especially under certain ventilation conditions (constant and equal fluid flow during inspiration and expiration; 1:1 ratio between inspiration and expiration), the alveolar pressure is minimally dependent on the imaginary component of the impedance, meaning that the alveolar pressure is determinable with high accuracy only from the real component of the impedance.

Flow-controlled ventilation (FCV; e.g., DE 10 2016 103 678.1 and DE 10 2016 109 528.1) is a mode of ventilation that has now also been clinically implemented, in which (in contrast to conventional ventilators) the gas flow is controlled and regulated not only during inspiration, but also during expiration. In the case of FCV, the expiratory gas outflow corresponds especially to the inspiratory gas inflow; this results in a ratio of inspiration to expiration of preferably 1:1. The gas flow (fluid flow) is stable or constant (i.e., does not exhibit any relevant change in absolute value) and is preferably just high enough for normoventilation to be achieved in the patient. Especially at the start of expiration, i.e., starting from the peak inspiratory pressure, the second fluid flow is preferably reduced (e.g., by a resistance). During expiration and especially toward the end of expiration, i.e., toward the end-expiratory pressure, the second fluid flow is then increasingly assisted (e.g., by suction).

Only one other ventilation method in which the expiratory gas outflow can be modulated is known, this method being experimental (but not yet clinically available): in the case of "FLow-controlled EXpiration" (FLEX; see Minerva Anestesiologica 80 (1): 19-28 (2014)), some control of expiration is achieved by a passive, dynamic resistor, which is arranged in the exhalation limb of a conventional ventilator and the resistance of which is gradually reduced during expiration. Depending on the restoring forces of the thorax/lung system and the expiratory (total) resistance, this system can modulate the gas outflow, but it cannot create and maintain a (largely) stable expiratory gas outflow. An I:E ratio of 1:1 and thus an inspiratory and expiratory gas flow (fluid flow) that is equal in absolute value is not possible either.

Compared to FLEX, the advantage of FCV is that the expiratory fluid flow is actively regulated (in the sense of a stable or constant gas flow) and thus known or always adjustable. This can, for example, be achieved with an active, dynamic resistor (e.g., combination of a resistance element with suction, e.g., by a gas-flow reversal element, e.g., known from DE 10 2007 013 385.7). For example, in a (temporally) first half of expiration, the particularly high fluid flow due to the restoring forces of the thorax/lung system is initially reduced by a resistance element. In a (temporally) second half of expiration, when the restoring forces become smaller and the fluid flow would thus usually gradually decrease, the fluid flow is increased by suction (e.g., a negative-pressure connection or the like) and kept constant overall.

Especially in the (temporally) second half of expiration, the gas outflow (second fluid flow) is thus very stable and can be adjusted in terms of absolute value especially according to the inspiratory gas inflow (first fluid flow), i.e., especially over the entire expiration process.

Compared to ventilation methods that operate with gas flow which decelerates during inspiration and/or expiration (e.g., VCV, i.e., volume-controlled ventilation, with gas flow regulated only during inspiration, or PCV, i.e., pressure-controlled ventilation, with gas flow likewise regulated only during inspiration), FCV creates optimal conditions for the measurements and calculations described here.

For a very accurate calculation of the (global) alveolar pressure or pressure plot, preference is given to an inspiratory and expiratory fluid flow which is stable or constant and is especially equal in absolute value. Only FCV meets these requirements.

For other reasons as well (e.g., mechanical- and energy-related reasons), it is appropriate to ventilate with slow and even changes in pressure and volume using the region of individually optimal, i.e., maximal, compliance.

FCV is especially intended for controlled ventilation with maximal lung protection, but not for assisting spontaneous breathing, since this requires distinctly higher gas flows.

Differences with respect to gas distribution in the lung can be minimized (within what is physically possible) especially through a fluid flow which is as low and stable as possible and is equal in absolute value during inspiration and expiration. CT scans and electrical impedance tomography have already demonstrated an overall better and more homogeneous ventilation of both healthy and diseased lungs by FCV.

It is thus especially an aim of the invention to describe a ventilator or method that allows an accurate (within what is physically possible) determination of indices or parameters (e.g., the ascertainment of the (global) alveolar pressure or pressure plot and of the airway-related and tissue-related resistance) during the controlled ventilation of a patient.

The ventilator is especially a ventilator which ventilates with a fluid flow which is continuous (without any relevant pauses) and is stable or constant and is equal in absolute value during inspiration and expiration (and thus an I:E ratio of typically 1:1), preferably in the region of optimal or maximal compliance. The fluid flow is just high enough to achieve normoventilation or the desired degree of carbon dioxide elimination or exhalation in the patient.

A user or preferably an (automatically operating) control device of the ventilator can, taking into account an ascertained or additionally estimated plot of at least a section of a compliance curve in a pressure-volume diagram, determine a position of a pressure interval having the pressures $P_I$ and $P_E$ and set these pressures on the ventilator (e.g., PIP as $P_I$ or as the first pressure and PEEP as $P_E$ or as the third pressure), so that at least a ventilation process, i.e., an inspiration and/or an expiration, occurs between these pressures $P_I$ and $P_E$ and an absolute value of the compliance of this ventilation process is as large as possible as a result over the resultant $V_T$. Alternatively, the position of a pressure interval having the pressures $P_I$ and $P_E$ can also be ascertained in a volume-pressure diagram. Moreover, the ventilation process should be set in such a way that a minute volume required for normoventilation can be supplied and discharged at maximum possible compliance, since an (optimally) large $V_T$ with an (optimally) low ventilation frequency increases the efficiency of carbon dioxide elimination and the airway or tissue of the patient is thus stressed as little as possible.

Although the inspiratory and expiratory fluid flow can differ in absolute value, what is especially envisaged is just a deviation of the current fluid flow from a set fluid flow or average fluid flow by at most 10%, preferably at most 5%, particularly preferably at most 1%, during the inspiration process and during the expiration process. In particular, a relevant deviation is also possible between the inspiration process and the expiration process. In particular, however, the ratio between inspiration process and expiration process is 1:1, i.e., the fluid flow is constant and is equal in absolute value for the inspiration process and the expiration process.

By means of the ventilator or by means of the method, it is possible to ascertain and optionally output (e.g., on a display of the ventilator) the mentioned indices or parameters (airway-related and tissue-related resistance and (global) alveolar pressure or pressure plot) on the basis of the measured values of the pressure and on the basis of the inspiratory or expiratory fluid flow (which is possibly actively controlled and is thus known at each time point).

There is further proposed a method for determining at least an alveolar pressure or a plot of an alveolar pressure of a patient by means of a ventilator, especially by means of the described ventilator.

The ventilator at least comprises a gas supply device and a gas discharge device, for supplying an (inspiratory) first fluid flow to an airway of a patient and for discharging an (expiratory) second fluid flow from the airway (of the patient) back into the ventilator or to an environment, a pressure sensor for sensing a pressure in the airway, and a control device for operating the ventilator. The control device is configured to carry out the method comprising at least the following steps:

a) defining a pressure interval in which the patient is to be ventilated for a defined time interval;
b) repeatedly and alternately carrying out one inspiration process at a time with a first fluid flow $Q_1$ by means of the gas supply device and one expiration process at a time with a second fluid flow $Q_2$ by means of the gas discharge device within the pressure interval,
c) (measuring or determining or) sensing the fluid flows and the pressure which changes during step b);
d) carrying out a Fourier transform for the sensed values of the pressure and forming a first frequency spectrum for the pressure and carrying out a Fourier transform for the sensed values of the fluid flows and forming a second frequency spectrum for the fluid flows;
e) calculating an impedance $Z_{aw}$ of the airway by dividing the first frequency spectrum by the second frequency spectrum, wherein the impedance comprises a real component Real($Z_{aw}$) and an imaginary component Im($Z_{aw}$);
f) modeling at least the real component by a first mathematical model and ascertaining an alveolar pressure or a plot of an alveolar pressure.

The above (nonexhaustive) division of the method steps into a) to f) is primarily intended for the purpose of differentiation only and does not impose any order and/or dependency. The frequency of the method steps, for example during the configuration and/or operation of the ventilator, can vary, too. It is also possible that method steps temporally overlap at least in part. Very particularly preferably, method steps a) to c) take place one after the other. However, it is also possible to repeat method steps a) to c) multiple times (i.e., for example for different pressure intervals). Step d)

can in particular be carried out after steps a) to c) have been carried out once or else after steps a) to c) have been carried out multiple times. Steps e) and f) are carried out in particular after step d). In particular, steps a) to f) are carried out in the order cited.

In particular, the ventilator is suitably designed for sole ventilation of the patient, wherein normoventilation of the patient is carried out via the control device at least before step a).

In particular, the ventilator comprises a suction device, so that in step b) the second fluid flow is at least partially generated by suction in at least an expiration process.

In particular, the fluid flow has been adjusted to a constant value at least during an inspiration process and an expiration process; wherein the first fluid flow $Q_1$ and the second fluid flow $Q_2$ are both constant during step b).

There is further proposed a control device for a ventilator, especially for the described ventilator, that is (suitably) equipped, configured or programmed to carry out the described method.

The discussions relating to the ventilator are applicable especially to the method and to the control device and vice versa in each case.

Furthermore, the described method can also be carried out manually (in part) by a user or semiautomatically or (fully) automatically by a (separate) computer or with a processor of a control device.

Accordingly, there is also proposed a data processing system comprising a processor which is adapted, programmed and configured in such a way that it carries out the described method or some of the steps of the method (with or without communication with a user).

There can be provided a computer-readable storage medium comprising commands/algorithms which, when executed by a computer/processor, cause said computer/processor to carry out the described method or at least some of the steps of the method (with or without communication with a user).

The use of indefinite articles ("a", "an"), especially in the claims and in the description reproducing said claims, should be understood as such and not as a numeral. Terms or components correspondingly introduced thereby are therefore to be understood in such a way that they are present at least once and can in particular, however, also be present multiple times.

As a precautionary measure, it should be noted that the numerals used here ("first", "second", . . . ) are primarily used (only) to distinguish between multiple objects, variables or processes of the same kind, i.e., in particular do not absolutely specify any dependency and/or order of these objects, variables or processes in relation to one another. Should a dependency and/or order be necessary, this is explicitly indicated here or it is obvious to a person skilled in the art upon studying the embodiment specifically described. If a component can occur multiple times ("at least one"), the description in relation to one of these components can apply equally to all or part of the plurality of these components; however, this is not mandatory.

Figure 2:
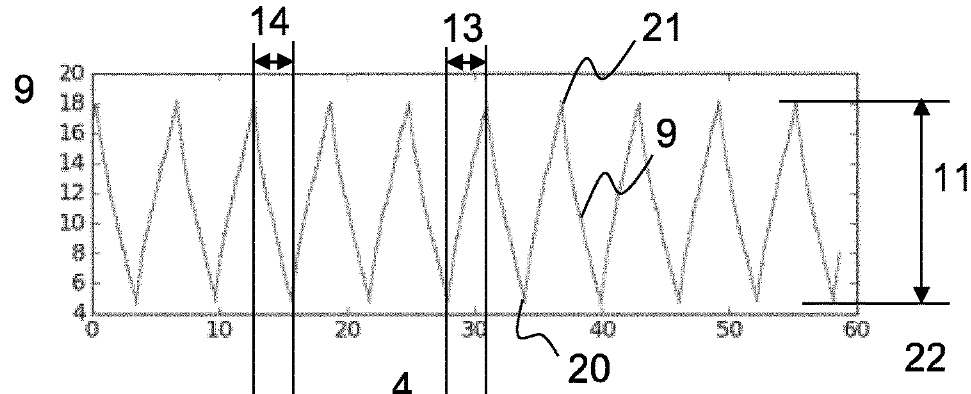
Figure 3:
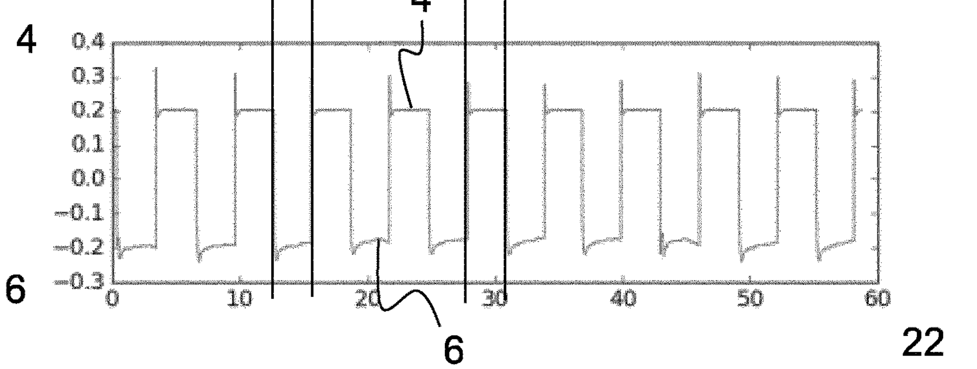
Figure 4:
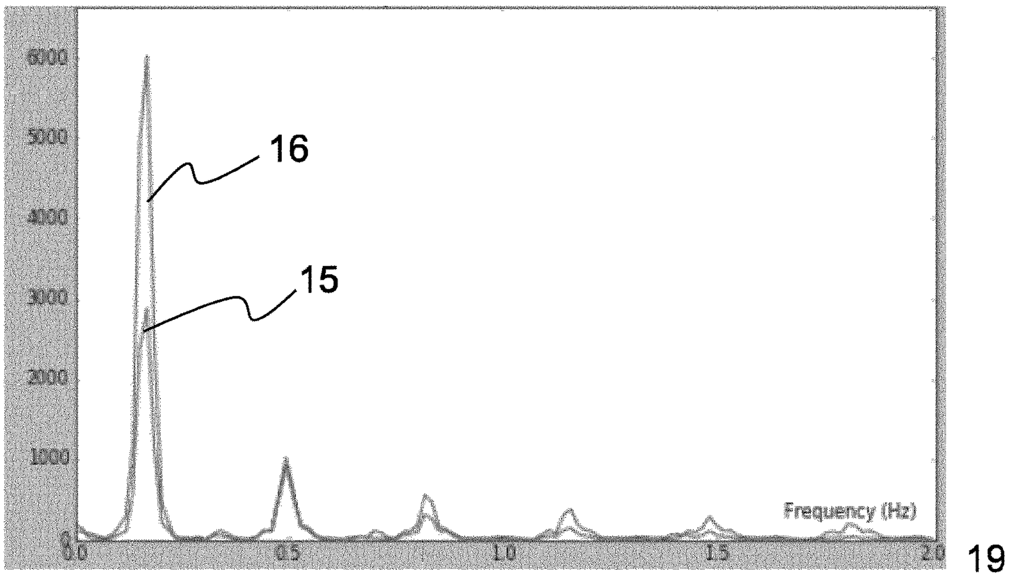
Figure 5:
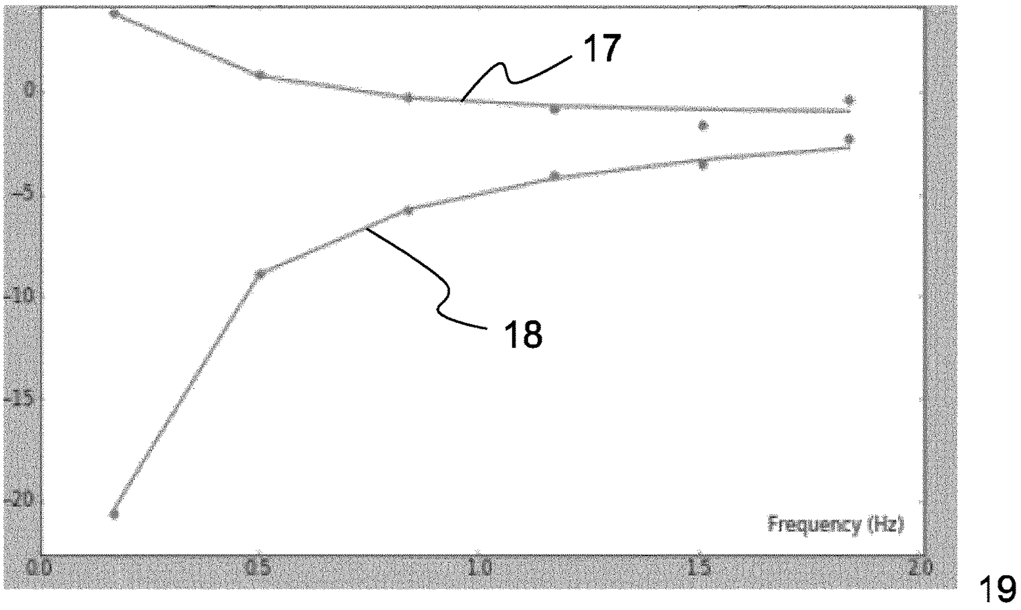
Figure 6:
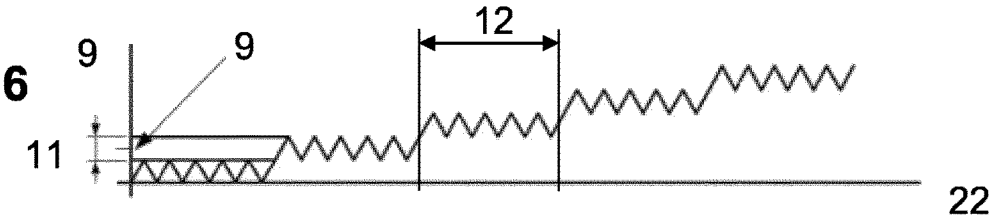

The invention and the technical environment will be more particularly elucidated below with reference to the accompanying figures. It should be noted that the invention is not to be limited by the exemplary embodiments cited. In particular, unless explicitly stated otherwise, it is also possible to extract partial aspects of the facts elucidated in the figures and to combine them with other parts and findings from the present description. In particular, it should be noted that the figures and in particular the proportions depicted are only schematic. In the figures:

FIG. 1: shows a ventilator in operation;

FIG. 2: shows a diagram containing a plot of a pressure during a ventilation process;

FIG. 3: shows a diagram containing a plot of a fluid flow during the ventilation process according to FIG. 2;

FIG. 4: shows a diagram containing frequency spectra of the ventilation process according to FIGS. 2 and 3;

FIG. 5: shows a diagram containing the components of the complex impedance of the frequency spectra according to FIG. 4; and FIG. 6: shows a diagram containing the plot of a pressure while carrying out the method.

FIG. 1 shows a ventilator 1 in operation. The ventilator 1 comprises a gas supply device 2 and a gas discharge device 3, for supplying an (inspiratory) first fluid flow 4 to an airway 5 of a patient and for discharging an (expiratory) second fluid flow 6 from the airway 5 back into the ventilator 1 or into the environment 7, a pressure sensor 8 for sensing a pressure 9 in the airway 5, and a control device 10 for operating the ventilator 1. The fluid flow 4, 6 can be adjusted to a constant value during an inspiration process 13 and an expiration process 14. The control device 10 is suitably designed to operate the ventilator 1 and to carry out the measurement method.

The pressure sensor 8 is arranged endotracheally. The pressure sensor 8 is located at the distal end of a ventilation catheter, which is arranged in the airway 5 of the patient as part of the ventilator 1.

The ventilator 1 also comprises a visualization device 24 (e.g., a display) on which the (total) resistance, airway-related resistance and tissue-related resistance, but especially also the current alveolar pressure 9 over time 22 and/or the plot of alveolar pressure 9 and volume 23 (as a pressure-volume curve) are depictable.

FIG. 2 shows a diagram containing a plot of a pressure 9 during a ventilation process. FIG. 3 shows a diagram containing a plot of a fluid flow 4, 6 during the ventilation process according to FIG. 2. FIGS. 2 and 3 will be described together in what follows. Reference is made to the discussions relating to FIG. 1.

Pressure 9 in [mbar] is plotted on the vertical axis of the diagram according to FIG. 2. Fluid flows 4, 6 in [liters/second] are plotted on the vertical axis of the diagram according to FIG. 3. Time 22 is plotted on the horizontal axes of the diagrams.

According to step a) of the method, what takes place is defining a pressure interval 11 in which the patient is to be ventilated for a defined time interval 12 (not defined here). According to step b), what takes place is repeatedly and alternately carrying out one inspiration process 13 at a time with a first fluid flow $Q_1$ 4 by means of the gas supply device 2 and one expiration process 14 at a time with a second fluid flow $Q_2$ 6 by means of the gas discharge device 3 within the pressure interval 11. According to step c), what takes place is sensing the fluid flows 4, 6 and the pressure 9 which changes during step b).

Ventilation is done continuously (i.e., without any relevant pauses) with fluid flows 4, 6 which are stable or constant and are equal in absolute value during inspiration and expiration (and thus an I:E ratio of typically 1:1), preferably in the region of optimal or maximal compliance. The fluid flow 4, 6 is just high enough to achieve normoventilation or the desired degree of carbon dioxide elimination or exhalation in the patient.

It can be seen that there is a ventilation frequency of approx. 0.167 Hz, i.e., five ventilation processes are carried out in 30 seconds.

FIG. 4 shows a diagram containing frequency spectra 15, 16 of the ventilation process according to FIGS. 2 and 3. FIG. 5 shows a diagram containing the components 17, 18 of the complex impedance of the frequency spectra 15, 16 according to FIG. 4. Reference is made to the discussions relating to FIGS. 1 to 3.

According to step d), what takes place is carrying out a Fourier transform for the sensed values of the pressure 9 and forming a first frequency spectrum 15 for the pressure 9 and carrying out a Fourier transform for the sensed values of the fluid flows 4, 6 and forming a second frequency spectrum 16 for the fluid flows 4, 6. It can be seen that the frequency spectra 15, 16 have clearly recognizable local maxima, for example at the ventilation frequency 19, i.e., at 0.167 Hz, and at multiples of the ventilation frequency 19, i.e., at 3×ventilation frequency 19, at 5×ventilation frequency, at 7×ventilation frequency 19, at 9×ventilation frequency 19, etc.

According to step e), what takes place is calculating an impedance $Z_{aw}$ of the airway 5 by dividing the first frequency spectrum 15 by the second frequency spectrum 16, wherein the impedance comprises a real component Real($Z_{aw}$) 17 and an imaginary component Im($Z_{aw}$) 18.

The impedance is respectively ascertained for the frequencies 19 that generate the local maxima. FIG. 5 depicts the values of the individual components 17, 18 for the respective frequency 19. The thus ascertained individual values of the components 17, 18 of the impedance, or points in the diagram, can then be approximated or modeled according to step f) by a curve, i.e., by a first mathematical model.

According to step f), what thus takes place is modeling at least the real component 17 by a first mathematical model and ascertaining an alveolar pressure 9 or a plot of an alveolar pressure 9.

In particular, the first model comprises the equation $\mathrm{Real}(Z_{aw})=R_{aw}+G/\omega^{\alpha}$, with $R_{aw}$: airway-related resistance;

$G/\omega^{\alpha}$: tissue-related resistance; with G as a constant, ω as the angular frequency (i.e., 2×π×frequency of ventilation) and α as a constant; wherein the real component 17 describes the resistance, i.e., the resistances of the airway 5 to be overcome during inspiration or expiration.

The alveolar pressure 9 $P_a$iv or the plot thereof is ascertained from the equation $P_{alv}=P_{trach}-Q_i\times R_{aw}$, with $Q_i$: the current fluid flow 4, 6 during step b) (see FIG. 3).

The measured or determined pressure 9 $P_{trach}$ is the pressure 9 in the airway 5 that changes over time 22 (see FIG. 2). The plot of the pressure 9 $P_{alv}$ over time 22 thus arises as a function of the pressure 9 $P_{trach}$ that changes over time 22.

In particular, the imaginary component 18 (see FIG. 5) is also modelable in step f) by a second mathematical model, wherein the second model comprises the equation $$Z_{aw} = R_{aw} + k \times j \times \omega \times I_{aw} + \frac{G - j \times H}{\omega^{\alpha}}; \text{ where}$$

$$\mathrm{Im}(Z_{aw}) = j \times \left(k \times \omega \times I_{aw} + \frac{-H}{\omega^{\alpha}}\right);$$

with k: a constant;

$I_{aw}$: inertia of the airway 5;

$-H/\omega^{\alpha}$: resilience of the airway 5 with H as a constant;

wherein the imaginary component 18 describes the airway reactance $X_a$, wherein a compliance of the airway 5 is described by $$C = -\frac{1}{\omega \times X_a}.$$

The imaginary component 18 should in particular not be ascertained for the determination of the alveolar pressure 9 or the plot thereof. However, other parameters that may be considered relevant can be derived from the imaginary component 18, for example airway reactance and compliance of the airway 5.

FIG. 6 shows a diagram containing the plot of a pressure 9 while carrying out the method. Pressure 9 in [mbar] is plotted on the vertical axis of the diagram. Time 22 is plotted on the horizontal axis. Reference is made to the discussions relating to FIGS. 1 to 5.

It is preferred that the pressure interval 11 is reduced at least for a time interval 12, the method being carried out within said time interval 12.

Steps a) to c) are carried out repeatedly here, i.e., multiple different pressure intervals 11 are defined one after the other and values for pressure 9 and fluid flows 4, 6 are then sensed in said pressure intervals 11 according to step c). Said values from different pressure intervals 11 are then further processed in steps d) to f).

In each step b), five inspiration processes 13 and expiration processes 14 (cf. FIG. 2) are carried out.

Each pressure interval 11 is associated with an average pressure 9, with the pressure interval 11 being limited by a pressure 9 PEEP (positive end-expiratory pressure) in an end-expiratory state 20 and by a pressure 9 PIP (peak inspiratory pressure) in an end-inspiratory state 21.

The pressure interval 11 encompasses, for example, at most 5 mbar, with only a small volume 23 of the fluid being supplied or discharged with each ventilation process. For example, the volume 23 of the fluid supplied and/or discharged within the pressure interval 11 and within one ventilation process is at most 10% of a maximum volume of the airway 5.

Here, five pressure intervals 11 are defined one after the other, the patient being ventilated with the ventilator 1 and the different pressure intervals being applied to the airway 5 in direct succession.

LIST OF REFERENCE SIGNS

1 Ventilator
2 Gas supply device
3 Gas discharge device
4 First fluid flow
5 Airway
6 Second fluid flow
7 Environment
8 Pressure sensor
9 Pressure
10 Control device
11 Pressure interval
12 Time interval
13 Inspiration process
14 Expiration process

15 First frequency spectrum

16 Second frequency spectrum

17 Real component

18 Imaginary component

19 Frequency

20 End-expiratory state

21 End-inspiratory state

22 Time

23 Volume

24 Visualization device

The invention claimed is:

1. A ventilator, at least comprising a gas supply device and a gas discharge device, for supplying a first fluid flow to an airway of a patient and for discharging a second fluid flow from the airway back into the ventilator or to an environment, a pressure sensor for sensing a pressure $P_{trach}$ in the airway, and a control device for operating the ventilator; wherein the control device is configured to carry out a method comprising:

a) defining a pressure interval in which the patient is to be ventilated for a defined time interval;

b) repeatedly and alternately carrying out one inspiration process at a time with the first fluid flow $Q_1$ by means of the gas supply device and one expiration process at a time with the second fluid flow $Q_2$ by means of the gas discharge device within the pressure interval, c) sensing fluid flows consisting of the first fluid flow and the second fluid flow, and the pressure which changes during step b);

d) carrying out a Fourier transform for sensed values of the pressure and forming a first frequency spectrum for the pressure and carrying out a Fourier transform for the sensed values of the fluid flows and forming a second frequency spectrum for the fluid flows;

e) calculating an impedance $Z_{aw}$ of the airway by dividing the first frequency spectrum by the second frequency spectrum, wherein the impedance comprises a real component $\mathrm{Real}(Z_{aw})$ and an imaginary component $\mathrm{Im}(Z_{aw})$; and f) modeling at least the real component by a first mathematical model and ascertaining an alveolar pressure $P_{alv}$ or a plot of an alveolar pressure $P_{alv}$;

wherein the first model comprises an equation $$\mathrm{Real}(Z_{aw}) = R_{aw} + \frac{G}{\omega^{\alpha}},$$

with $R_{aw}$: airway-related resistance;

$G/\omega^{\alpha}$: tissue-related resistance; with G as a constant, $\omega$ as an the angular frequency and $\alpha$ as a constant; and wherein the real component describes the resistance to be overcome during inspiration or expiration.

2. The ventilator as claimed in claim 1, wherein the alveolar pressure $P_{alv}$ is ascertained from an equation $P_{alv}=P_{trach}-Q_i \times R_{aw}$; with $Q_i$: a current fluid flow.

3. The ventilator as claimed in claim 1, wherein the imaginary component is also modelable in step f) by a second mathematical model, wherein the second model comprises the equation $$Z_{aw} = R_{aw} + k \times j \times \omega \times I_{aw} + \frac{G - j \times H}{\omega^{\alpha}};\ \text{where}$$

$$\mathrm{Im}(Z_{aw}) = j \times \left(k \times \omega \times I_{aw} + \frac{-H}{\omega^{\alpha}}\right);$$

with k: a constant; $I_{aw}$: inertia of the airway;

$$\frac{-H}{\omega^{\alpha}}:$$

resilience of the airway with H as a constant; wherein the imaginary component describes an airway reactance $X_a$, wherein a compliance of the airway is described by $$C = -\frac{1}{\omega \times X_a}.$$

4. The ventilator as claimed in claim 1, wherein the pressure sensor is arranged endotracheally.

5. The ventilator as claimed in claim 1, wherein at least steps a) to c) are carried out in different pressure intervals.

6. The ventilator as claimed in claim 1, wherein the pressure interval encompasses at most 10 mbar.

7. The ventilator as claimed in claim 1, wherein a fluid volume supplied or discharged within the pressure interval is at most 10% of a maximum volume of the airway.

8. The ventilator as claimed in claim 1, wherein at least five inspiration processes and expiration processes are carried out in step b).

9. The ventilator as claimed in claim 1, wherein values for the pressure and the fluid flow are sensed at same time points in each case in step c) and the time points have time intervals of at most 0.1 seconds.

10. The ventilator as claimed in claim 1, wherein the ventilator is suitably designed for sole ventilation of the patient; wherein normoventilation of the patient is performable via the control device at least before step a) or after step c).

11. The ventilator as claimed in claim 1, wherein the gas discharge device comprises a suction device, so that in step b) the second fluid flow is at least partially generated by suction in at least an expiration process.

12. The ventilator as claimed in claim 1, wherein the fluid flows are adjustable to a constant value at least during an inspiration process and an expiration process; wherein the first fluid flow $Q_1$ and the second fluid flow $Q_2$ are both constant during step b).

13. The ventilator as claimed in claim 12, wherein the fluid flows are of equal size.

14. A method for determining at least an alveolar pressure $P_{alv}$ or a plot of an alveolar pressure $P_{alv}$ of a patient by means of a ventilator, wherein the ventilator at least comprises a gas supply device and a gas discharge device, for supplying a first fluid flow to an airway of a patient and for discharging a second fluid flow from the airway back into the ventilator or to an environment, a pressure sensor for sensing a pressure $P_{trach}$ in the airway, and a control device for operating the ventilator; wherein the control device is configured to carry out the method comprising:

a) defining a pressure interval in which the patient is to be ventilated for a defined time interval;

b) repeatedly and alternately carrying out one inspiration process at a time with a first fluid flow $Q_1$ by means of the gas supply device and one expiration process at a time with a second fluid flow $Q_2$ by means of the gas discharge device within the pressure interval, c) sensing fluid flows consisting of the first fluid flow and the second fluid flow, and the pressure which changes during step b);

d) carrying out a Fourier transform for sensed values of the pressure and forming a first frequency spectrum for the pressure and carrying out a Fourier transform for the sensed values of the fluid flows and forming a second frequency spectrum for the fluid flows;

e) calculating an impedance $Z_{aw}$ of the airway by dividing the first frequency spectrum by the second frequency spectrum, wherein the impedance comprises a real component Real($Z_{aw}$) and an imaginary component Im($Z_{aw}$); and f) modeling at least the real component by a first mathematical model and ascertaining an alveolar pressure $P_{alv}$ or a plot of an alveolar pressure $P_{alv}$;

wherein the first model comprises an equation $$\text{Real}(Z_{aw}) = R_{aw} + \frac{G}{\omega^{\alpha}}, \text{ with } R_{aw}:$$

airway-related resistance;

$$\frac{G}{\omega^{\alpha}}:$$

tissue-related resistance; with G as a constant, ω as an angular frequency and α as a constant; and wherein the real component describes the resistance to be overcome during inspiration or expiration.

15. The method as claimed in claim 14, wherein the ventilator is suitably designed for sole ventilation of the patient; wherein normoventilation of the patient is carried out via the control device at least before step a).

16. The method as claimed in claim 14, wherein the gas discharge device comprises a suction device, so that in step b) the second fluid flow is at least partially generated by suction in at least an expiration process.

17. The method as claimed in claim 14, wherein the fluid flows have been adjusted to a constant value at least during an inspiration process and an expiration process; wherein the first fluid flow $Q_1$ and the second fluid flow $Q_2$ are both constant during step b).

18. A control device for a ventilator that is equipped, configured or programmed to carry out the method as claimed in claim 14.

* * * * *